United States Patent [19]

Kleemann et al.

[11] Patent Number: 5,719,169
[45] Date of Patent: Feb. 17, 1998

[54] SUBSTITUTED BENZOYLGUANIDINES, THEIR USE AS A MEDICAMENT OR DIAGNOSTIC, AND MEDICAMENT CONTAINING THEM

[75] Inventors: Heinz-Werner Kleemann, Bad Homburg; Hans-Jochen Lang, Hofheim; Jan-Robert Schwark, Frankfurt am Main; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 674,991

[22] Filed: Jul. 3, 1996

Related U.S. Application Data

[63] Continuation of Ser. No. 281,576, Jul. 28, 1994, abandoned.

[30] Foreign Application Priority Data

Jul. 31, 1993 [DE] Germany .................... 43 25 822.0

[51] Int. Cl.[6] .......................... C07D 213/02; A61K 31/44
[52] U.S. Cl. .......................... 514/357; 514/400; 514/407; 514/427; 546/332; 548/336.1; 548/375.1; 548/561
[58] Field of Search .......................... 546/332; 548/336.1, 548/375.1, 501; 514/357, 400, 407, 427; 424/9

[56] References Cited

U.S. PATENT DOCUMENTS

| | | | |
|---|---|---|---|
| 3,780,027 | 12/1973 | Cragoe et al. | 269/239.6 |
| 5,091,394 | 2/1992 | Englert et al. | 514/331 |
| 5,292,755 | 3/1994 | Englert et al. | 514/331 |

FOREIGN PATENT DOCUMENTS

| | | | |
|---|---|---|---|
| 2111386 | 6/1994 | Canada | 546/332 |

OTHER PUBLICATIONS

Derwent Abstract of WO 93/04048, 1993.

A. Schömig et al., "Inhibition of $Na^+/H^+$ exchange suppresses noradrenaline release and arrhythmias in the ischemic rat heart," Eur. Heart J. 9(suppl. 1): 167 (1988), Book of abstracts.

*Primary Examiner*—Zinna Northington Davis
*Attorney, Agent, or Firm*—Finnegan, Henderson, Farabow, Garrett & Dunner, L.L.P.

[57] ABSTRACT

The invention relates to benzoylguanidines of the formula I:

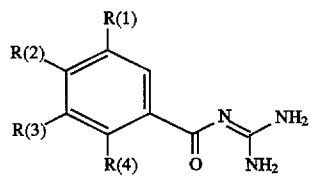

to pharmaceutically acceptable salts of these compounds and to a process for preparing compounds of the formula I, which comprise reacting a compound of the formula II

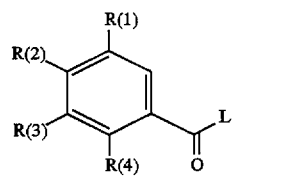

with guanidine. The compounds of the invention are suitable as antiarrhythmic pharmaceuticals having a cardioprotective component for the prophylaxis and treatment of infarction and for the treatment of angina pectoris.

20 Claims, No Drawings

SUBSTITUTED BENZOYLGUANIDINES, THEIR USE AS A MEDICAMENT OR DIAGNOSTIC, AND MEDICAMENT CONTAINING THEM

This application is a continuation of application Ser. No. 08/281,576, filed Jul. 28, 1994, now abandoned which application is entirely incorporated herein by reference.

The invention relates to benzoylguanidines of the formula I

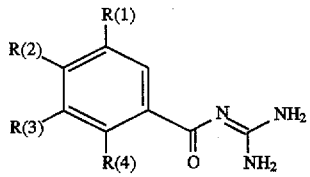

in which:

R(1) is hydrogen, F, Cl, Br, I, —$NO_2$, —C≡N, —$X_o$—$(CH_2)_p$—$(CF_2)_q$—$CF_3$, R(5)—$SO_m$—, R(6)—CO—, R(6)R(7)N—CO— or R(6)R(7)N—$SO_2$—;

X is oxygen, —S— or NR(14);

m is zero, 1 or 2;

o is zero or 1;

p is zero, 1 or 2;

q is zero, 1, 2, 3, 4, 5 or 6;

R(5) and R(6) are
($C_1$–$C_8$)-alkyl, ($C_3$–$C_6$)-alkenyl, —$C_nH_{2n}$—R(8) or $CF_3$;

n is zero, 1, 2, 3 or 4;

R(8) is ($C_3$–$C_7$) -cycloalkyl, or phenyl which is unsubstituted or substituted by 1 to 3 substituents selected from the group consisting of F, Cl, $CF_3$, methyl, methoxy and NR(9)R(10); R(9) and R(10) are H or ($C_1$–$C_4$) -alkyl;

or

R(6) is hydrogen;

R(7) is hydrogen or ($C_1$–$C_4$)-alkyl; or

R(6) and R(7) together can be 4 or 5 methylene groups, of which one $CH_2$ group can be replaced by oxygen, S, NH, N—$CH_3$ or N-benzyl;

R(2) is

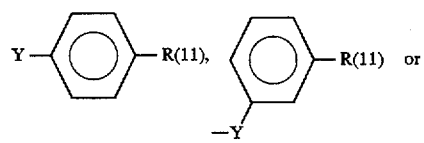

R(11) is ($C_1$–$C_9$) -heteroaryl which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;

Y is oxygen, —S— or NR(12);

R(12) is H or ($C_1$–$C_4$) -alkyl;

R(3) is defined as R(1); or

R(3) is ($C_1$–$C_6$)-alkyl or —X—R(13);

X is oxygen, —S— or NR(14);

R(14) is H or ($C_1$–$C_3$) -alkyl;

R(13) is H, ($C_1$–$C_6$) -alkyl, ($C_3$–$C_8$) -cycloalkyl, —$C_bH_{2b}$—R(15) where b is zero, 1, 2, 3 or 4; or R(13) and R(14) can also together be 4 or 5 methylene groups, of which one $CH_2$ group can be replaced by oxygen, S, NH, N—$CH_3$ or N-benzyl;

R(15) is phenyl which is unsubstituted or substituted by 1–3 substituents selected from the group consisting of F, Cl, $CF_3$, methyl, methoxy and NR(9)R(10);

R(9) and R(10) are H or ($C_1$–$C_4$)-alkyl;

R(4) is hydrogen, —OR(16), —NR(16)R(17) or $C_rF_{2r+1}$;

R(16) and R(17) independently are hydrogen or ($C_1$–$C_3$) -alkyl;

r is 1, 2, 3 or 4;

as well as pharmaceutically tolerated salts thereof.

Compounds of the formula I are preferred in which:

R(1) is hydrogen, F, Cl, —C≡N, —$CF_3$, R(5)—$SO_m$—, R(6)—CO—, R(6)R(7)N—CO— or R(6)R(7)N—$SO_2$—;

m is zero, 1 or 2;

R(5) and R(6) are ($C_1$–$C_8$)-alkyl, ($C_3$–$C_4$)-alkenyl, —$C_nH_{2n}$—R(8), —$CF_3$;

n is zero or 1;

R(8) is ($C_3$–$C_6$)-cycloalkyl or phenyl, which is unsubstituted or substituted by 1–3 substituents from the group consisting of F, Cl, $CF_3$, methyl, methoxy and NR(9)R(10); R(9) and R(10) are H or methyl;

or

R(6) is alternatively hydrogen;

R(7) is hydrogen or methyl;

R(3) is hydrogen, methyl, cyano, —$CF_3$, F or Cl;

and the other radicals are defined as above, as well as pharmaceutically tolerated salts thereof.

Compounds I are particularly preferred in which:

R(1) is hydrogen, F, Cl, —C≡N, —$CF_3$, R(5)—$SO_m$—, R(6)—CO—,

R(6)R(7)N—CO— or R(6)R(7)N—$SO_2$—;

m is zero, 1 or 2;

R(5) is methyl or $CF_3$;

R(6) and R(7) independently of one another are hydrogen, methyl or $CF_3$;

R(2) is

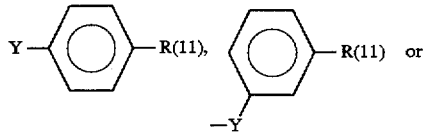

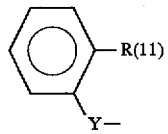

R(11) is ($C_1$–$C_9$)-heteroaryl which is linked via C or N and which is tmsubstituted or substituted by 1 to 2 radicals selected from the group consisting of F, Cl, $CF_3$, $CH_3$, methoxy, dimethylamino and benzyl;

Y is oxygen, —S— or NR(12)—;

R(12) is hydrogen or methyl;

R(3) is methyl, cyano, trifluoromethyl, F, Cl or hydrogen;

R(4) is hydrogen, OH, $NH_2$ or $CF_3$;

as well as pharmaceutically tolerated salts thereof.

Compounds of the formula I are particularly preferred in which:

R(1) is hydrogen, F, Cl, —C≡N, —CF₃, R(5)—SO₂, R(6)—CO—,
R(6)R(7)N—CO— or R(6)R(7)N—SO₂—;

R(5) is methyl or CF₃;

R(6) and R(7) independently of one another are hydrogen, methyl or CF₃;

R(2) is

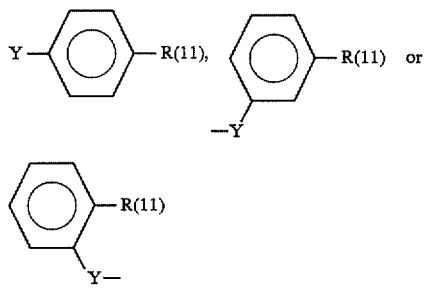

R(11) is (C₁–C₅)-heteroaryl which is linked via C or N and which is unsubstituted or substituted by 1 to 2 radicals selected from the group consisting of F, Cl, CF₃, CH₃, methoxy, dimethylamino and benzyl;

Y is oxygen, —S— or NR(12)—; R(12) is hydrogen or methyl;

R(3) is methyl, cyano, trifluoromethyl, F, Cl or hydrogen;
R(4) is hydrogen, OH, NH₂ or CF₃;

as well as pharmaceutically tolerated salts thereof.

Compounds of the formula I are very particularly preferred in which: R(1) is hydrogen, F, Cl, —C≡N, —CF₃, R(5)—SO_m—, R(6)—CO—, R(6)R(7)N—CO— or R(6)R(7)N—SO₂—;

R(5) is methyl or CF₃;

R(6) and R(7) independently of one another are H, methyl or CF₃;

R(2) is

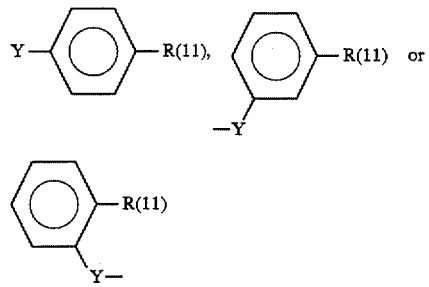

R(11) is pyrrolyl, imidazolyl, pyrazolyl, pyridyl which is unsubstituted or substituted by 1 to 2 radicals selected from the group consisting of F, Cl, CF₃, CH₃, methoxy, dimethylamino and benzyl;

Y is oxygen, —S— or NR(12)—;
R(12) is hydrogen or methyl;
R(3) is methyl, cyano, trifluoromethyl, F, Cl or hydrogen;
R(4) is hydrogen, OH, NH₂ or CF₃;

as well as pharmaceutically tolerated salts thereof.

The designated alkyl radicals can be either straight-chain or branched.

(C₁–C₉)-Heteroaryl is understood to mean radicals which are derived from phenyl or naphthyl, in which one or more CH groups are replaced by N and/or in which at least two neighboring CH groups (with the formation of a five-membered aromatic ring) are replaced by S, NH or O. In addition, one or both the atoms of the fusion site of bicyclic radicals (as in indolizinyl) can also be N atoms.

It applies, in particular, that heteroaryy is furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl.

In addition, the invention relates to a process for preparing the compound I, which comprises reacting compounds of the formula II

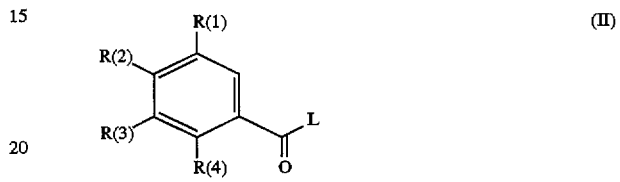

where R(1) to R(4) have the given meaning and L is a leaving group which can readily be substituted nucleophilically, with guanidine and optionally converting the product into a pharmacologically tolerated salt.

The activated acid derivatives of the formula II, in which L is an alkoxy, preferably a methoxy, group, a phenoxy group, a phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OH), for example using thionyl chloride.

In addition to the carbonyl chlorides of the formula II (L=Cl), further activated acid derivatives of the formula II can also be prepared, in a manner known per se, directly from the underlying benzoic acid derivatives (formula II, L=OB), such as, for example, the methyl esters of the formula II with L=OCH₃ by treating with gaseous HCl in methanol, the imidazolides of the formula II by treating with carbonyldiimidazole [L=1-imidazolyl, Staab, Angew. Chem. Int. Ed. Engl. 1, 351–367 (1962)], the mixed anhydrides II with Cl—COOC₂H₅ or tosyl chloride in the presence of triethylamine in an inert solvent, as well as the activation of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Weiss and Krommer, Proceedings of the 21st European Peptide Symposium, Peptides 1990, Editors E. Geralt and D. Andreu, Escom, Leiden, 1991]. A series of suitable methods for preparing activated carboxylic acid derivatives of the formula II are given, with citation of the source literature, in J. March, Advanced Organic Chemistry, Third Edition (John Wiley & Sons, 1985), p. 350.

The reaction of an activated carboxylic acid derivative of the formula II with guanidine is effected, in a manner known per se, in a protic or aprotic organic solvent which is polar but inert. In this context, methanol, isopropanol or THF have proven to be suitable, at temperatures of from 20° C. up to the boiling temperature of these solvents, for use in the reaction of the methyl benzoates (II, L=OMe) with guanidine. Aprotic, inert solvents, such as THF, dimethoxyethane and dioxane, were advantageously employed in most of the reactions of compounds II with salt-free guanidine. However, water can also be used, while employing a base, such as, for example, NaOH, as solvent in the reaction of II with guanidine.

When L=Cl, an acid scavenger, e.g. in the form of excess guanidine, is advantageously added in order to bind the hydrohalic acid.

Some of the underlying benzoic acid derivatives of the formula II are known and are described in the literature. The unknown compounds of the formula II may be prepared by methods known from the literature by converting, for example, 4-(or 5-)halo-3-chlorosulfonylbenzoic acids with ammonia or amines to 3-aminosulfonyl-4-(or 5-)halobenzoic acids or with a weak reductant such as sodium bisulfite and subsequent alkylation to 3-alkylsulfonyl-4-(or 5-)halobenzoic acids and reacting the resulting benzoic acids to give compounds I according to the invention in accordance with one of the above-described process variants.

The introduction of some substituents in the 4 and 5 positions is achieved by methods known from the literature involving palladium-mediated cross-coupling of aryl halides or aryl triflates with, for example, organostannanes, organoboronic acids or organohoranes or organocopper or organozinc compounds.

Benzoylguanidines I are in general weak bases and are able to bind acid with the formation of salts. Salts of all pharmacologically tolerated acids, for example halides, in particular hydrochlorides, lactates, sulfates, citrates, tartrates, acetates, phosphates, methanesulfonates and p-toluenesulfonates, are suitable acid addition salts.

The compounds I are substituted acylguanidines. The most prominent representative of the acylguanidines is the pyrazine derivative amiloride, which is used in therapy as a potassium-sparing diuretic agent. Numerous further compounds of the amiloride type are described in the literature, such as, for example, dimethylamiloride or ethylisopropylamiloride.

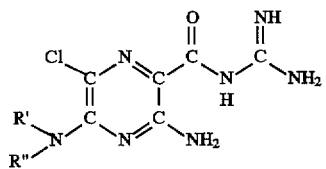

Amiloride: R', R"=H
Dimethylamiloride: R', R"=CH$_3$
Ethylisopropylamiloride: R'=CH$_2$H$_5$,R"=CH(CH$_3$)$_2$ In addition to this, investigations have become known which point to amiloride having antiarrhythmic properties (Circulation 79, 1257 to 1263 (1989)). However, a factor counting against any widespread use of amiloride as an antiarrhythmic agent is that this effect is only weakly expressed and is accompanied by hypotensive and saluretic effects, which latter side effects are undesirable when treating cardiac arrhythmias.

Indications that amiloride has antiarrhythmic properties were also obtained in experiments on isolated animal hearts (Eur. Heart J. 9 (suppl.1): 167 (1988) (book of abstracts)). Thus it was found, using rat hearts, for example, that amiloride was able to completely suppress artificially induced ventricular fibrillation. The above-mentioned mentioned amiloride derivative ethylisopropylamiloride was even more potent than amiloride in this model system.

Benzoylguanidines which do not carry a hydrogen atom in the position corresponding to the radical R(1) are described in the U.S. Pat. No. 5,091,394 (HOE 89/F 288). German Patent Application P 42 04 575.4 (HOE 92/F 034) proposes 3,5-substituted benzoylguanidines in which the substituent R(2), however, does not have meanings claimed according to the present invention.

In U.S. Pat. No. 3,780,027, acylguanidines are claimed which are structurally similar to the compounds of the formula I and which are derived from commercially available loop diuretics, such as bumetanide. Correspondingly, these compounds have been reported to have strong salidiuretic activity.

It was surprising, therefore, that the compounds according to the invention do not exhibit any undesirable and disadvantageous salidiuretic properties, but exhibit very good antiarrhythmic properties against arrhythmias of the type that occur, for example, in association with symptoms of oxygen deficiency. As a consequence of their pharmacological properties, the compounds are outstandingly suitable for use as antiarrhythmic pharmaceuticals having a cardioprotective component for the prophylaxis and treatment of infarction as well as for the treatment of angina pectoris, the compounds also inhibiting or strongly reducing, in a preventive manner, the pathophysiological processes in association with the occurrence rence of ischemically induced damage, in particular in association with the elicitation of ischemically induced cardiac arrhythmias. On account of their protective effects against pathological hypoxic and ischemic situations, the compounds of the formula I according to the invention can be used, as a consequence of inhibition of the cellular Na$^+$/H$^+$ exchange mechanism, as pharmaceuticals for treating all acute or chronic damage elicited by ischemia, or diseases which are primarily or secondarily induced thereby. This applies to their use as pharmaceuticals for surgical interventions, e.g. in association with organ transplantations, it being possible sible to use the compounds to protect the organs in the donor before and during removal and to protect removed organs, for example when being treated with physiological bathing fluids or when being stored in these fluids, and also in association with transfer of the organs into the recipient body. The compounds are likewise valuable protective pharmaceuticals for use when carrying out angioplastic surgical interventions, for example on the heart or on peripheral vessels. In accordance with their protective action against ischemically induced damage, the compounds are also suitable for use as pharmaceuticals for treating ischemias of the nervous system, in particular of the CNS, e.g. for the treatment of stroke or of cerebral edema. In addition to this, the compounds of formula I according to the invention are likewise suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the vasculature. For this reason, the compounds of the formula I are suitable, as valuable therapeutic agents, for use in diseases in which cell proliferation represents a primary or secondary cause, and may therefore be used as antiatherosclerotic agents, and as agents against diabetic secondary complications, carcinomatous disorders, fibrotic disorders, such as pulmonary fibrosis, hepatic fibrosis or renal fibrosis, and against organ hypertrophy and hyperplasia, in particular in hyperplasia or hypertrophy of the prostate.

The compounds according to the invention are efficacious inhibitors of the cellular sodium/proton antiporter (Na$^+$/H$^+$ exchanger), which, in numerous disorders (essential hypertension, atherosclerosis, diabetes, etc.), is also elevated in cells of the type which are readily accessible to measurement, such as, for example, in erythrocytes, blood platelets or leukocytes. The compounds according to the invention are therefore suitable for use as outstanding, simple, scientific tools, for example in their employment as diagnostic agents for determining and differentiating particular forms of hypertension, but also for use in atherosclerosis, diabetes, proliferative disorders, and so on. In addition, the compounds of formula I are suitable for use in preventive therapy for preventing the genesis of high blood pressure, for example of essential hypertension.

In comparison with the known compounds, the compounds according to the invention have a significantly improved solubility in water. They are therefore considerably better suited to i.v. administration.

In this context, pharmaceuticals which contain a compound I can be administered orally, parentsrally, intravenously or rectally, or by inhalation, the preferred route of administration being dependent on how the disorder manifests itself. In this context, the compounds I may be used alone or together with pharmaceutical auxiliary substances, both in the case of veterinary medicine and in the case of human medicine.

Owing to his specialist knowledge, the person skilled in the art is familiar with which auxiliary substances are suitable for the desired pharmaceutical formulation. In addition to solvents, gel-formers, suppository bases, tablet auxiliary substances, and other active-compound carriers, antioxidants, dispersants, emulsifiers, defoamers, taste corrigents, preservatives, solubilizers or dyes, for example, can be used.

In order to prepare a form for oral use, the active compounds are mixed with the additives which are suitable for the purpose, such as excipient substances, stabilizers or inert diluents, and converted by the customary methods into the forms suitable for administration, such as tablets, coated tablets, hard gelatin capsules or aqueous, alcoholic or oily solutions. Gum arabic, magnesia, magnesium carbonate, potassium phosphate, lactose, glucose or starch, in particular corn starch, for example, can be used as inert excipients. In this context, the preparation can be effected as dry or wet granules. Vegetable or animal oils, for example, such as sunflower oil or cod-liver oil, are suitable for use as oily excipient substances or as solvents.

For subcutaneous or intravenous administration, the active compounds, if desired together with the substances which are customary for the purpose, such as solubilizers, emulsifiers or additional auxiliary substances, are brought into solution, suspension or emulsion. Examples of suitable solvents are: water, physiological saline solution, or alcohols, for example ethanol, propanol or glycerol, and in addition sugar solutions as well, such as glucose or mannitol solutions, or else a mixture of the different solvents mentioned.

Solutions, suspensions or emulsions, for example, of the active compound of the formula I in a pharmaceutically harmless solvent, such as, in particular, ethanol or water, or a mixture of such solvents, are suitable for use as a pharmaceutical formulation for administration in the form of aerosols or sprays.

Depending on requirements, the formulation can also contain other further pharmaceutical auxiliary substances, such as surfactants, emulsifiers or stabilizers, as well as propellant. Such a preparation customarily contains the active compound in a concentration of about 0.1 to 10, in particular of about 0.3 to 3% by weight.

The dosage of the active compound of the formula I to be administered, and the frequency of the administration, depend on the strength and the duration of the effect of the compounds used, additionally also on the nature and severity of the disease to be treated, as well as on the sex, age, weight and individual responsiveness of the mammal to be treated.

On average, the daily dose of a compound of the formula I for a patient of about 75 kg in weight is at least 0.001 mg/kg, preferably 0.01 mg/kg, up to at most 10 mg/kg, preferably 1 mg/kg, of body weight. In acute episodes of the illness, for example immediately after suffering a cardiac infarction, even higher, and in particular more frequent, dosages may also be necessary, e.g. up to 4 individual doses per day. In association with i.v. use in particular, for example in the case of an infarction patient in intensive care, up to 200 mg per day may be necessary.

List of abbreviations:

| | |
|---|---|
| MeOH | methanol |
| DMF | N,N-dimethylformamide |
| NBS | N-bromosuccinimide |
| AIBN | $\alpha,\alpha$-azobisisobutyronitrile |
| EI | electron impact |
| DCI | desorption-chemical ionization |
| RT | room temperature |
| EA | ethyl acetate (EtOAc) |
| DIP | diisopropyl ether |
| MTB | methyl tertiary-butyl ether |
| M.p. | melting point |
| HEP | n-heptane |
| DME | dimethoxyethane |
| FAB | fast atom bombardment |
| $CH_2Cl_2$ | dichloromethane |
| THF | tetrahydrofuran |
| eq. | equivalent |
| ES | electrospray ionization |

Experimental section

General instructions for preparing benzoylguanidines (I) Variant A: from benzoic acids (II, L=OH)

0.01 mol of the benzoic acid derivative of the formula II is dissolved or suspended in 60 ml of anhydrous THF and 1.78 g (0.011 mol) of carbonyldiimidazole are then added. After stirring at RT for 2 hours, 2.95 g (0.05 mol) of guanidine are introduced into the reaction solution. After stirring overnight, the THF is distilled off under reduced pressure (Rotavapor) and water is added to the mixture, which is then adjusted to pH 6 to 7 using 2N HCl, and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

General instructions for preparing benzoylguanidines (I) Variant B: from alkyl benzoates (II, L=O-alkyl)

5 mmol of the alkyl benzoate of the formula II and 25 mmol of guanidine (free base) are dissolved in 15 ml of isopropanol or suspended in 15 ml of THF and heated under reflux (typical reaction time 2 to 5 hours) until conversion is complete (thin-layer monitoring). The solvent is distilled off under reduced pressure (Rotavapor) and the residue is taken up in 300 ml of EA and washed 3 times using 50 ml of $NaHCO_3$ solution each time. Drying takes place over $Na_2SO_4$, the solvent is distilled off in vacuo, and the residue chromatographed on silica gel using a suitable eluent, e.g. EA/MeOH 5:1. (Salt formation: cf. variant A)

EXAMPLE 1

4-(1- Benzylimidazol-2-yl)phenoxy-3-methylsulfonylhenzoylguanidine, dihydrochloride

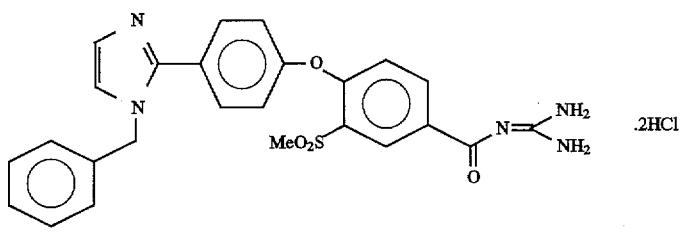

a) 4-(2-Methoxyethoxymethoxy)benzaldehyde 0.16 mol of 4-hydroxybenzaldehyde and 0.32 mol of ethyldiisopropylamine are dissolved in 250 ml of $CH_2Cl_2$ (anhydrous), and 0.24 mol of 2-methoxyethoxymethyl chloride are then added dropwise at room temperature. The mixture is stirred at this temperature for 2 hours, then the solvent is removed in vacuo. The residue is taken up using 200 ml of EA and the solution is washed once each with 200 ml of $Na_2CO_3$ solution and 200 ml of $NaH_2PO_4$ solution, dried over $Na_2SO_4$ and the solvent removed in vacuo. 34 g of a light brown oil are obtained, which is reacted further without purification.

$R_f$ (MTB)=0.53 MS (DCI): 211 (M+1)

b) 2-[4-(2-Methoxyethoxymethoxy)phenyl]imidazole 83 mmol of aldehyde 1a), 0.46 mol of 30% aqueous glyoxal solution and 0.39 mol of sodium acetate are dissolved at room temperature in 250 ml of saturated aqueous $NH_3$ solution and 500 ml of MeOH. The solution is allowed to stand at room temperature for 24 hours, then the MeOH is removed in vacuo, 200 ml of $Na_2CO_3$ solution are added and the mixture is extracted 3 times using 300 ml of EA each time. The organic phase is dried over $Na_2SO_4$ and the solvent is removed in vacuo. Chromatography on silica gel using EA/MeOH 10:1 yields 13 g of a crystalline product. M.p. 63° to 64° C.

Rf (EA/MeOH 10:1)=0.43 MS (DCI): 249 (M+1)

c) 1-Benzyl-2-[4-(2-methoxyethoxymethoxy)phenyl]-imidazole 11 mmol of imidazole 1b are dissolved in 50 ml of DMF and 11 mmol of NaH are added at room temperature. The mixture is stirred at this temperature for 30 minutes, 11 mmol of benzyl bromide are injected and the mixture is stirred at room temperature for a further 2 hours. It is then poured onto 200 ml of NaCl solution, extracted 3 times using 100 ml of MTB each time and dried over $Na_2SO_4$. The solvent is removed in vacuo, and chromatography on silica gel using $CH_2Cl_2$/MeOH 15:1 yields 3.8 g of a pale yellow oil.

$R_f$ ($CH_2Cl_2$/MeOH 15:1)=0.27 MS (DCI): 339 (M+1)

d) 1-Benzyl-2-(4-hydroxyphenyl)imidazole 10 mmol of the ether 1e) are dissolved in 200 ml of $CH_2Cl_2$ and the solution is treated dropwise at room temperature with 10 mmol of $TiCl_4$. It is stirred at room temperature for 24 hours, then $NaHCO_3$ solution is added dropwise until pH=7 is reached. The titanium dioxide is filtered off, the phases are separated and the aqueous phase is extracted a further 3 times with 200 ml of EA. The organic phases are combined and dried over $Na_2SO_4$, and the solvents are removed in vacuo. Chromatography on silica gel using EA/MeOH 10:1 yields 1.1 g of a colorless foam.

$R_f$ (EA/MeOH 10:1)=0.35 MS (DCI): 251 (M+1)

e) Methyl 4-(1-benzylimidazol-2-yl)phenoxy-3-methylsulfonylbenzoate 3.6 mmol of phenol 1d), 3.6 mmol of methyl 4-fluoro-3-methylsulfonylbenzoate and 1.5 g of $K_2CO_3$ are stirred at 130° C. for 2 hours under argon in 40 ml of DMF (anhydrous). The mixture is allowed to cool, is poured onto 200 ml of $H_2O$ and is extracted 3 times using 200 ml of EA each time. The EA phase is additionally washed with 100 ml of $NaHCO_3$ solution and dried over $Na_2SO_4$, and the solvent is removed in vacuo. Chromatography on silica gel using EA yields 1.2 g of a colorless oil.

Rf (EA)=0.19 ME (ES): 463 (M+1)

f) 4-(1-Benzylimidazol-2-yl)phenoxy-3-methylsulfonylbenzoylguanidine, dihydrochloride 1.5 mml of ester 1e) and 7.5 mmol of guanidine are reacted in 10 ml of isopropanol according to variant B. 400 mg of colorless foam.

Rf (EA/MeOH 3:1)=0.22 MS (FAB): 490 (M+1)

EXAMPLE 2

4-(Imidazol-2-yl)phenoxy-3-methylsulfonylbenzoylguanidine, dihydrochloride

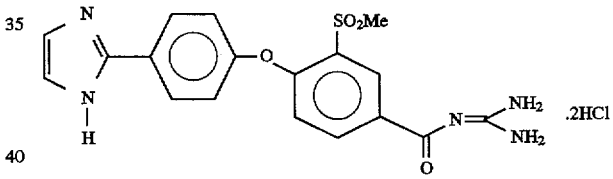

a) 2-Hydroxyethyl 4-(imidazol-2-yl)phenoxy-3-methylsulfonylbenzoate 1.4 mmol of N-benzylimidazole derivative 1e), 14 mmol of ammonium formate and 100 mg of Pd/C (10% Pd) are heated under reflux for 4 hours in 20 ml of ethylene glycol. The mixture is allowed to cool, is poured into 100 ml of $Na_2CO_3$ solution and is extracted 3 times using 50 ml of EA each time. It is dried over $MgSO_4$ and the solvent is removed in vacuo. Chromatography on silica gel using EA/MeOH 8:1 yields 400 mg of a colorless solid.

Rf (EA/MeOH 5:1)=0.40 MS (DCI): 403 (M+1)

b) 4-(Imidazol-2-yl)phenoxy-3-methylsulfonylbenzoylguanidine, dihydrochloride 0.5 mmol of ester 2a) and 2.5 mmol of guanidine are reacted according to variant B in 3 ml of isopropanol. 100 mg, m.p. 210° C. (dec.)

Rf (EA/MeOH 5:1)=0.06 MS (ES): 400(M+1)

EXAMPLE 3

4-(3-Pyridylphenoxy)-3-methylsulfonylbenzoylguanidine, dihydrochloride

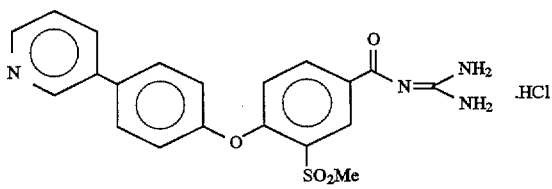

a) 4-(3-Pyridyl)anisole 5 mmol of 3-bromopyridine are dissolved in 30 ml of toluene and 8 ml of ethanol and 0.25 mmol of $(CH_3COO)_2$Pd, 0.5 mmol of triphenylphosphene, 5 ml of a 2N aqueous $Na_2CO_3$ solution and 5.5 mmol of 4-methoxyphenylboronic acid are added. The mixture is heated under reflux for 30 minutes, then cooled and poured onto 100 ml of $NaHCO_3$ solution. It is then extracted 3 times using 100 ml of EA each time and dried over $Na_2SO_4$, the solvent is removed in vacuo and the residue is chromatographed on silica gel using MTB. 720 mg of a colorless oil are obtained.

Rf (EA)=0.46 MS (DCI): 186 (M+1)

b) 4-(3-Pyridyl)phenol 3.7 mmol of anisole 3a) are heated to reflux for 3 hours in 10 ml of glacial acetic acid and 10 ml of 48% aqueous HBr solution. After cooling, the mixture is poured onto 150 ml of $Na_2CO_3$ solution and extracted 3 times using 150 ml of EA each time. It is dried over $Na_2SO_4$ and the solvent is removed in vacuo. 580 mg of pale yellow crystals are obtained, which are used without further purification. M.p. 197° C.

$R_f$ (MTB)=0.34 MS (DCI): 172 (M+1)

c) Methyl 4-[4-(3-pyridyl)phenoxy]-3-methylsulfonylbenzoate 3.1 mmol of methyl 4-bromo-3-methylsulfonylbenzoate, 3.1 mmol of phenol 3b) and 9.3 mmol of $K_2CO_3$ are stirred at 130° C. for 3 hours in 30 ml of DMF (anhydrous). After cooling, the mixture is poured onto 70 ml of $Na_2CO_3$ solution and extracted 3 times using 100 ml of EA each time. It is dried over $Na_2SO_4$, the solvent is removed in vacuo and the residue is chromatographed on silica gel using EA. 890 mg of white crystals are obtained, m.p. 145° to 146° C.

Rf (EA)=0.40 MS (DCI): 384 (M+1)

d) 4-[4-(3-Pyridyl)phenoxy]-3-methylsulfonylbenzoylguanidine, dihydrochloride 2.2 mmol of ester 3c) are converted into the acylguanidine according to variant B. 190 mg of white crystals, m.p. 270° C.

Rf (EA/MeOH 10:1)=0.14 MS (ES): 411 (M+1)

The title compounds of Examples 4 to 6 are synthesized analogously to Example 3:

EXAMPLE 4

4-[4-(4-Pyridyl)phenoxy]-3-methylsulfonylbenzoylguanidine, dihydrochloride

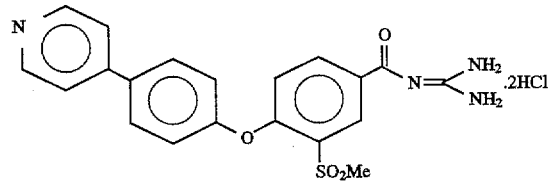

M.p. 178° to 179° C.

Rf (EA/MeOH 5:1)=0.29 ME (ES): 411 (M+1)

EXAMPLE 5

4-[4-(2-Pyridyl)phenoxy]-3-methylsulfonylbenzoylguanidine, dihydrochloride

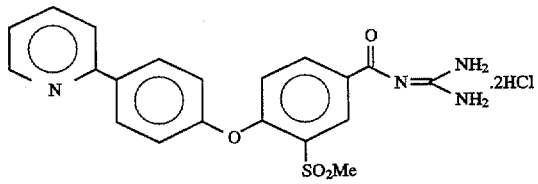

M.p. 220° to 223° C.

Rf (EA/MeOH 5:1)=0.44 MS (ES): 411 (M+1)

EXAMPLE 6

4-[4-(2,6-Bistrifluoromethylpyridin-4-yl)phenoxy]-3-methylsulfonoylbenzoylguanidine, dihydrochloride

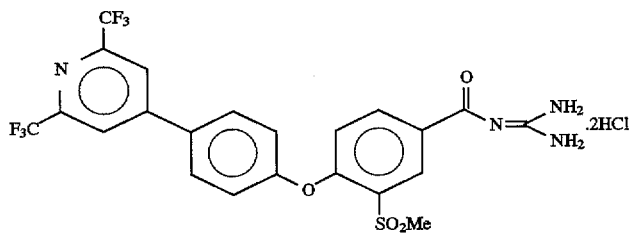

M.p. 267° C.

$R_f$ (EA)=0.26 MS (ES): 547 (M+1)

a) 2,6-Bistrifluoromethyl-4-bromopyridine 4 mmol of 2,6-bistrifluoromethyl-4-chloropyridine are dissolved in 20 ml of 33% HBr in glacial acetic acid and the solution is stirred at 100° C. for 10 hours. It is poured onto 100 ml of $Na_2CO_3$ solution and extracted 3 times using 100 ml of diethyl ether each time. The solvent is carefully removed under normal pressure, and 940 mg of a colorless liquid are obtained which is used without further purification as described under 3a).

Example 7 was synthesized analogously to Example 2:

EXAMPLE 7

3-(Imidazol-2-yl)phenoxy-3-methylsulfonylbenzoylguanidine, dihydrochloride

M.p. >200° C. (decomposition)
$R_f$ (EA/MeOH 3:1)=0.18 MS (ES): 400 (M+1)
Pharmacological data:
Inhibition of the $Na^+/H^+$ exchanger of rabbit erythrocytes New Zealand White rabbits (Ivanovas) received a standard diet containing 2% cholesterol for six weeks in order to activate the $Na^+/H^+$ exchange and thus to be able to determine, by flame photometry, the $Na^+$ influx into the erythrocytes via $Na^+/H^+$ exchange. The blood was removed from the aural arteries and rendered incoagulable using 25 IU of potassium heparin. A part of each sample was used for the duplicate determination of the hematocrit by means of centrifugation. Aliquots of in each case 100 µl were used for measuring the initial $Na^+$ content of the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl) aminomethane). The erythrocytes were then washed three times with ice-cold $MgCl_2$/ouabain solution (mmol/ml: 112 $MgCl_2$, 0.1 ouabain) and hemolyzed in 2.0 ml of distilled water. The intracellular sodium content was determined by flame photometry.

The net influx of $Na^+$ was calculated from the difference between the initial sodium values and the sodium content of the erythrocytes following incubation. The amiloride-inhibitable sodium influx was calculated from the difference in the sodium content of the erythrocytes following incubation with and without amiloride $3 \times 10^{-4}$ mol/l. This method was also employed in the case of the compounds according to the invention.

Results
Inhibition of the $Na^+/H^+$ exchanger:

| Example | $IC_{50}$ (mol/l) |
|---------|-------------------|
| 1 | $3.0 \times 10^{-7}$ |
| 2 | $3.0 \times 10^{-7}$ |
| 3 | $2.0 \times 10^{-7}$ |
| 5 | $3.0 \times 10^{-7}$ |

We claim:
1. A benzoylguanidine of the formula I in which:
R(1) is hydrogen, F, Cl, Br, I, $-NO_2$, $-C\equiv N$, $-X_o-(CH_2)_q-(CF_2)_p-CF_3$,
R(5)$-SO_m-$, R(6)$-CO-$, R(6)R(7)N$-CO-$ or R(6)R(7)N$-SO_2-$;
X is oxygen, $-S-$ or NR(14);
m is zero, 1 or 2;
o is zero or 1;
p is zero, 1 or 2;
q is zero, 1, 2, 3, 4, 5 or 6;
R(5) and R(6) are
($C_1$-$C_8$)-alkyl, ($C_3$-$C_6$)-alkenyl, $-C_n-H_{2n}-$R(8) or $CF_3$;
n is zero, 1, 2, 3 or 4;
R(8) is ($C_3$-$C_7$)-cycloalkyl, or phenyl which is unsubstituted or substituted by 1 to 3 substituents selected from the group consisting of
F, Cl, $CF_3$, methyl, methoxy and NR(9)R(10);
R(9) and R(10) are H or ($C_1$-$C_4$)-alkyl;
or
R(6) is hydrogen;
R(7) is H or ($C_1$-$C_4$)-alkyl;
or
R(6) and R(7) together may be 4 or 5 methylene groups, of which one $CH_2$ group may be replaced by oxygen, S, NH, N$-CH_3$ or N-benzyl;
R(2) is R(11) is ($C_1$-$C_9$)-heteroaryl which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;
Y is oxygen, $-S-$ or NR(12);
R(12) is H or ($C_1$-$C_4$)-alkyl;
R(3) is defined as R(1);
or
R(3) is ($C_1$-$C_6$)-alkyl or $-X-$R(13);
X is oxygen, $-S-$ or NR(14);
R(14) is hydrogen or ($C_1$-$C_3$)-alkyl;
R(13) is H, ($C_1$-$C_6$)-alkyl, ($C_3$-$C_8$)-cycloalkyl or $-C_b-H_{2b}-$R(15);
b is zero, 1, 2, 3 or 4;
or
R(13) and R(14) may together be 4 or 5 methylene groups, of which one $CH_2$ group may be replaced by oxygen, S, NH, N$-CH_3$ or N-benzyl;
R(15) is
phenyl which is unsubstituted or substituted by 1-3 substituents selected from the group consisting of F, Cl, $CF_3$, methyl, methoxy and NR(9)R(10);
R(9) and R(10) are H or ($C_1$-$C_4$)-alkyl;
R(4) is hydrogen, $-$OR(16), $-$NR(16)R(17) or $C_rF_{2r+1}$;
R(16) and R(17) independently are hydrogen or ($C_1$-$C_3$)-alkyl; r is 1, 2, 3 or 4;
or a pharmaceutically tolerated salt thereof.
2. A benzoylguanidine of the formula I as claimed in claim 1, in which:

R(1) is hydrogen, F, Cl, —C≡N, —CF₃, R(5)—SO$_m$—,
R(6)—CO—, R(6)R(7)N—CO— or R(6)R(7)N—SO₂—;

m is zero, 1 or 2;

R(5) and R(6) are (C₁-C₈)-alkyl, (C₃-C₄)-alkenyl, —C$_n$H$_{2n}$—R(8), —CF₃;

n is zero or 1;

R(8) is (C₃-C₆)-cycloalkyl or phenyl, which is unsubstituted or substituted by 1-3 substituents from the group consisting of F, Cl, CF₃, methyl, methoxy and NR(9)R(10) where R(9) and R(10) are H or methyl;

where

R(6) is H,

R(7) is H or methyl,

R(3) is hydrogen, methyl, cyano, —CF₃, F or Cl;

or a pharmaceutically tolerated salts thereof.

3. A benzoylguanidine of the formula I as claimed in claim 1, in which:

R(1) is hydrogen, F, Cl, —C≡N, —CF₃, R(5)—SO$_m$—,
R(6)—CO—, R(6)R(7)N—CO— or R(6)R(7)N—SO₂—;

m is zero, 1 or 2;

R(5) is methyl or CF₃;

R(6) and R(7) independently of one another are hydrogen, methyl or CF₃;

R(2) is

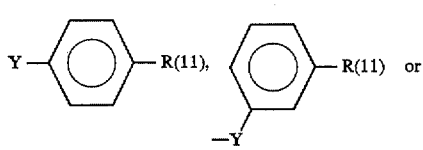, 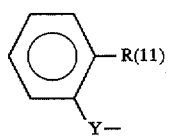

R(11) is (C₁-C₉)-heteroaryl which is linked via C or N and which is unsubstituted or substituted by 1 to 2 radicals selected from the group consisting of F, Cl, CF₃, CH₃, methoxy, dimethylamino and benzyl;

Y is oxygen, —S— or NR(12)—;

R(12) is hydrogen or methyl;

R(3) is methyl, cyano, trifluoromethyl, F, Cl or hydrogen;

R(4) is hydrogen, OH, NH₂ or CF₃;

or a pharmaceutically tolerated salt thereof.

4. A benzoylguanidine of the formula I as claimed in claim 1, in which:

R(1) is hydrogen, F, Cl, —C≡N, —CF₃, R(5)—SO₂,
R(6)—CO—, R(6)R(7)N—CO— or R(6)R(7)N—SO₂—;

R(5) is methyl or CF₃;

R(6) and R(7) independently of one another are hydrogen, methyl or CF₃;

R(2) is

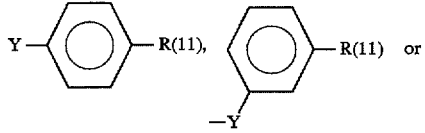

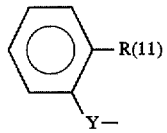

R(11) is (C₁-C₅)-heteroaryl which is linked via C or N and which is unsubstituted or substituted by 1 to 2 radicals selected from the group consisting of F, Cl, CF₃, CH₃, methoxy, dimethylamino and benzyl;

Y is oxygen, —S— or NR(12)—;

R(12) is hydrogen or methyl;

R(3) is methyl, cyano, trifluoromethyl, F, Cl or hydrogen;

R(4) is hydrogen, OH, NH₂ or CF₃;

or a pharmaceutically tolerated salt thereof.

5. A benzoylguanidine of the formula I as claimed in claim 1, in which:

R(1) is hydrogen, F, Cl, —C≡N, —CF₃, R(5)—SO₂—,
R(6)—CO—, R(6)R(7)N—CO— or R(6)R(7)N—SO₂—;

R(5) is methyl or CF₃;

R(6) and R(7) independently of one another are H or methyl;

R(2) is

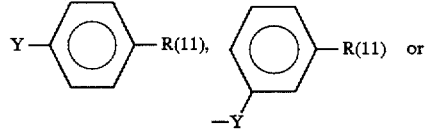

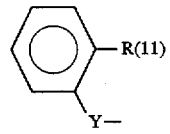

R(11) is pyrrolyl, imidazolyl, pyrazolyl, pyridyl which is unsubstituted or substituted by 1 to 2 radicals selected from the group consisting of F, Cl, CF₃, CH₃, methoxy, dimethylamino and benzyl;

Y is oxygen, —S— or NR(12)—;

R(12) is hydrogen or methyl;

R(3) is methyl, cyano, trifluoromethyl, F, Cl or hydrogen;

R(4) is hydrogen, OH, NH₂ or CF₃;

or a pharmaceutically tolerated salt thereof.

6. A pharmaceutical composition for the treatment of arrhythmias, which comprises an effective amount for said treatment of a compound of formula I as claimed in claim 1 together with a pharmaceutically acceptable carrier.

7. A method for the treatment of arrhythmias, which comprises administering to a host in need of said treatment an effective mount of a compound of the formula I as claimed in claim 1.

8. A method for the treatment or prophylaxis of cardiac infarction which comprises administering to a host in need of said treatment an effective amount of a compound of the formula I as claimed in claim 1.

9. A method for the treatment or prophylaxis of angina pectoris, which comprises administering to a host in need of said treatment an effective amount of a compound of the formula I as claimed in claim 1.

10. A method for the treatment or prophylaxis of ischemic conditions of the heart, which comprises administering to a host in need of said treatment an effective amount of a compound of the formula I as claimed in claim 1.

11. A method for the treatment or prophylaxis of ischemic conditions of the peripheral and central nervous systems and of stroke, which comprises administering to a host in need of said treatment an effective amount of a compound of the formula I as claimed in claim 1.

12. A method for the treatment or prophylaxis of ischemic conditions of peripheral organs and limbs, which comprises administering to a host in need of said treatment an effective amount of a compound of the formula I as claimed in claim 1.

13. A method for the treatment or prophylaxis of conditions of shock, which comprises administering to a host in need of said treatment an effective amount of a compound of the formula I as claimed in claim 1.

14. A pharmaceutical composition for use in surgical interventions and organ transplants, which comprises an effective amount of a compound of the formula I and a pharmaceutically acceptable carrier.

15. A method for the preservation and storage of transplants for surgical intervention, which comprises treating said transplants with an effective amount of a compound of formula I as claimed in claim 1.

16. A method for the treatment of diseases in which cell proliferation is a primary or secondary cause, which comprises administering to a host in need of said treatment an effective mount of a compound of formula I as claimed in claim 1.

17. A method according to claim 16, wherein said disease in which cell proliferation is a primary or secondary cause is atherosclerosis, a secondary complication of diabetes, a cancer, a fibrotic disorder or prostate hyperplasia.

18. A method according to claim 17, wherein said fibrotic disorder is pulmonary fibrosis, hepatic fibrosis or renal fibrosis.

19. A diagnostic agent for the inhibition of the $Na^+/H^+$ exchanger and the diagnosis of hypertension and proliferative disorders, which comprises an effective amount of a compound of claim 1 and a pharmaceutical acceptable carrier.

20. A pharmaceutical composition for the treatment of cardiac infarct, angina pectoris, ischemic heart conditions, ischemic conditions of the peripheral and central nervous systems, of stroke and of the peripheral organs and limbs, and of states of shock which comprises an effective mount of a compound of formula I as claimed in claim 1 together with a pharmaceutically acceptable carrier.

* * * * *

UNITED STATES PATENT AND TRADEMARK OFFICE
CERTIFICATE OF CORRECTION

PATENT NO.    : 5,719,169
DATED         : February 17, 1998
INVENTOR(S)   : Kleemann et al.

It is certified that error appears in the above-identified patent and that said Letters Patent is hereby corrected as shown below:

Claim 1, column 13, line 64, "CI" should read --Cl--.
Claim 1, column 14, lines 25-28, " 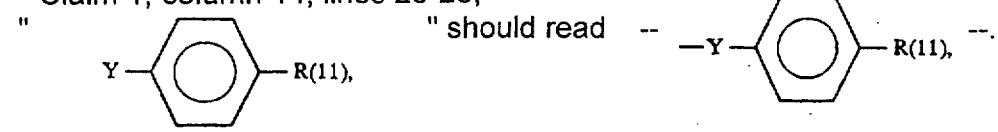 "

Claim 1, column 14, line 39, "CL" should read --Cl--.
Claim 2, column 15, line 20, "salts" should read --salt--.
Claim 3, column 15, lines 34-37, " 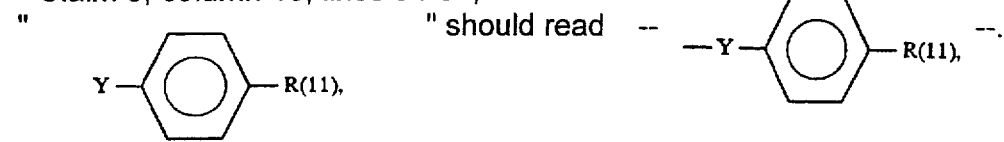 "

Claim 4, column 16, lines 3-6,

" 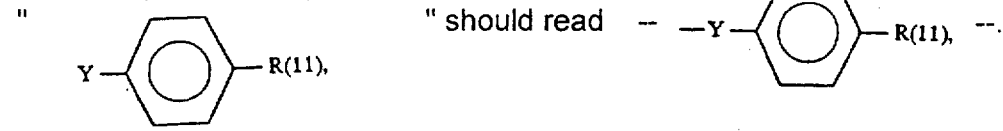 "

UNITED STATES PATENT AND TRADEMARK OFFICE
CERTIFICATE OF CORRECTION

PATENT NO.   : 5,719,169
DATED        : February 17, 1998
INVENTOR(S)  : Kleemann et al.

It is certified that error appears in the above-identified patent and that said Letters Patent is hereby corrected as shown below:

Claim 5, column 16, lines 34-37, 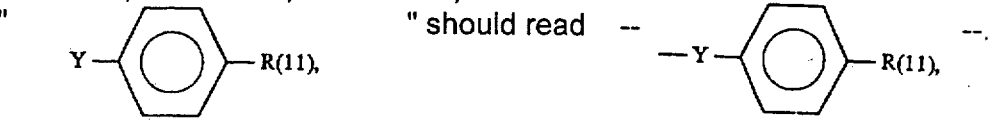

Claim 16, column 18, line 6, "mount" should read --amount--.
Claim 20, column 18, line 24, "mount" should read --amount--.

Signed and Sealed this

Twenty-sixth Day of September, 2000

Attest:

Q. TODD DICKINSON

*Attesting Officer*      *Director of Patents and Trademarks*